US009539297B2

(12) United States Patent
Andreas et al.

(10) Patent No.: US 9,539,297 B2
(45) Date of Patent: Jan. 10, 2017

(54) USE OF CYTOKINE-RELEASING, BIODEGRADABLE PARTICLES IN HYALURONIC ACID FOR THE TREATMENT OF CARTILAGE DEFECTS, IN PARTICULAR OF OSTEOARTHROSIS

(75) Inventors: Kristin Andreas, Berlin (DE); Jochen Ringe, Birkenwerder (DE); Michael Sittinger, Berlin (DE)

(73) Assignee: CHARITE—UNIVERSITATSMEDIZIN BERLIN, Berlin (DE)

( * ) Notice: Subject to any disclaimer, the term of this patent is extended or adjusted under 35 U.S.C. 154(b) by 28 days.

(21) Appl. No.: 13/990,643

(22) PCT Filed: Nov. 30, 2011

(86) PCT No.: PCT/EP2011/071412
§ 371 (c)(1),
(2), (4) Date: Sep. 9, 2013

(87) PCT Pub. No.: WO2012/072692
PCT Pub. Date: Jun. 7, 2012

(65) Prior Publication Data
US 2013/0337074 A1  Dec. 19, 2013

(30) Foreign Application Priority Data
Dec. 1, 2010  (DE) .......... 10 2010 062 288

(51) Int. Cl.
*A61K 38/02* (2006.01)
*A61K 31/728* (2006.01)
(Continued)

(52) U.S. Cl.
CPC ............ *A61K 38/02* (2013.01); *A61K 9/0019* (2013.01); *A61K 9/14* (2013.01); *A61K 9/1647* (2013.01);
(Continued)

(58) Field of Classification Search
CPC ........ A61K 38/02; A61K 9/14; A61K 9/0019; A61K 9/1647; A61K 31/728; A61K 38/195; A61K 38/363
(Continued)

(56) References Cited

U.S. PATENT DOCUMENTS 5,288,502 A  2/1994 McGinity et al.
6,428,804 B1  8/2002 Suzuki et al.
(Continued)

FOREIGN PATENT DOCUMENTS

DE  102007051059 A1  4/2009
WO  WO 0128591  4/2001
(Continued)

OTHER PUBLICATIONS

Microsphere: retrieved from internet: http://www.biology-online.org/dictionary/Microspherein. Retrieved on Feb. 9, 2015.*
(Continued)

*Primary Examiner* — Ernst V Arnold
*Assistant Examiner* — Hong Yu
(74) *Attorney, Agent, or Firm* — Fox Rothschild LLP

(57) ABSTRACT

The present invention relates to a composition comprising, or consisting of 2-50 mg/ml hyaluronic acid, 0.1-500 mg/ml of biodegradable particles with an average mean particle diameter of 1 nm-500 μm, 1 pg/ml-10 μg/ml cytokines, where the concentrations specified are based in each case on the total volume (w/v) of the composition and where the cytokines are enclosed in the biodegradable particles, and to their use in the treatment of cartilage defects, for example traumatic cartilage defects or osteoarthrosis.

15 Claims, 9 Drawing Sheets

Figure 1:
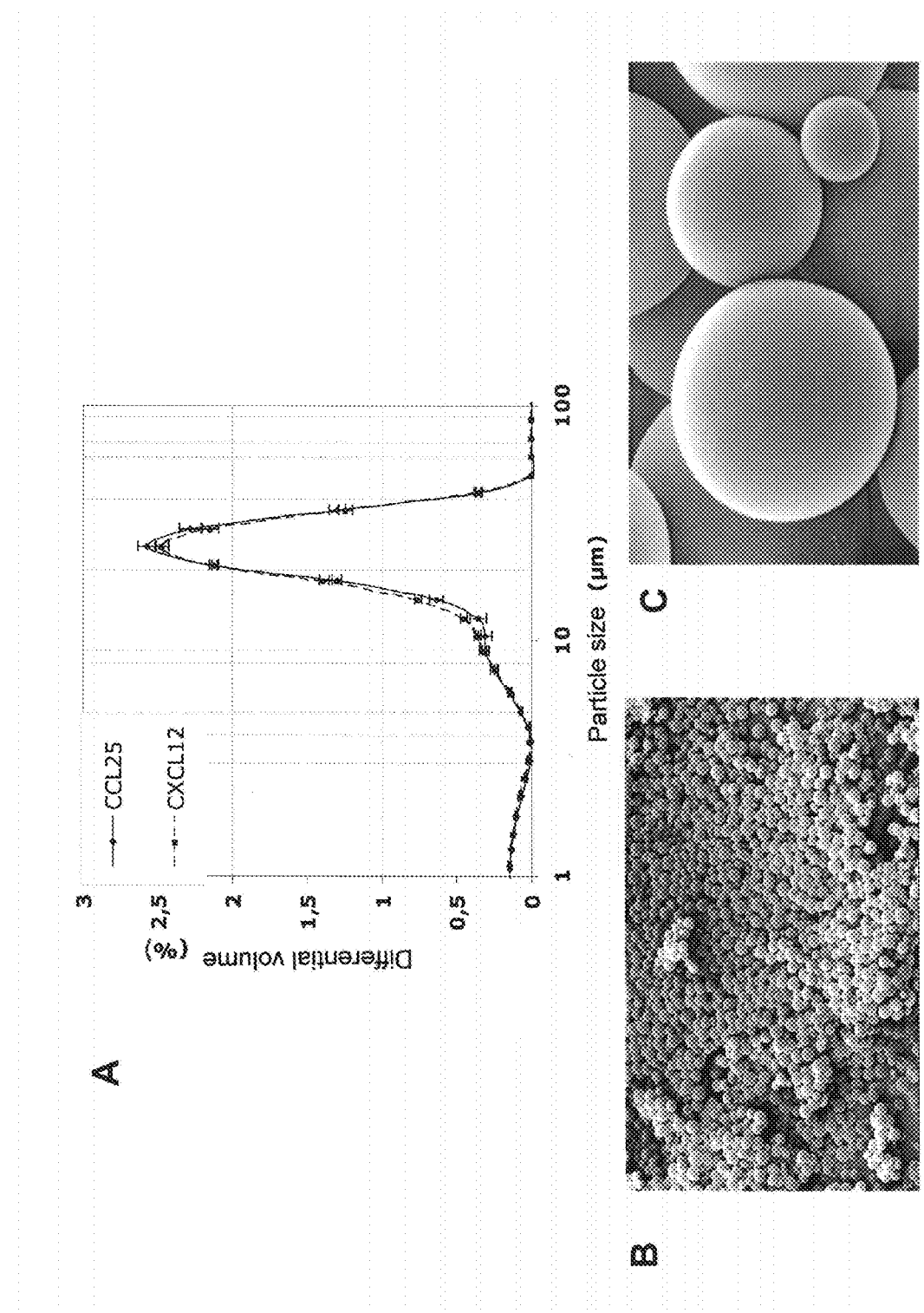

(51) Int. Cl.
  *A61K 9/14*  (2006.01)
  *A61K 9/00*  (2006.01)
  *A61K 9/16*  (2006.01)
  *A61K 38/19* (2006.01)
  *A61K 38/36* (2006.01)

(52) U.S. Cl.
  CPC ........... *A61K 31/728* (2013.01); *A61K 38/195* (2013.01); *A61K 38/363* (2013.01)

(58) Field of Classification Search
  USPC ................................ 424/499; 514/16.8, 17.1
  See application file for complete search history.

(56) References Cited

U.S. PATENT DOCUMENTS

2009/0043400 A1* 2/2009 Evans et al. ............... 623/23.76
2009/0148527 A1* 6/2009 Robinson ............. A61K 9/0048
                                              424/484

2010/0285113 A1  11/2010  Shoichet

FOREIGN PATENT DOCUMENTS

WO  WO 2005014027 A1     2/2005
WO  WO 2006106521 A2    10/2006
WO  WO 2010/100506 A1 *  9/2010
WO  WO 2010123900 A1    10/2010

OTHER PUBLICATIONS

Salamone: Polymeric Materials Encyclopedia, vol. 10, Q-S, CRC Press, 1996.*
International Search Report and Written Opinion dated Jun. 25, 2012 based on International Patent Application No. PCT/EP2011/071412, International Filing Date Nov. 30, 2011.
Hegewald et al., "Hyaluronic acid and autologous synovial fluid induce chondrogenic differentiation of equine mesenchymal stem cells: A preliminary study," Tissue and Cell, Churchill Livingstone Medical Journals, Edinburgh, GB (Dec. 1, 2004) 36(6): 431-438.

* cited by examiner

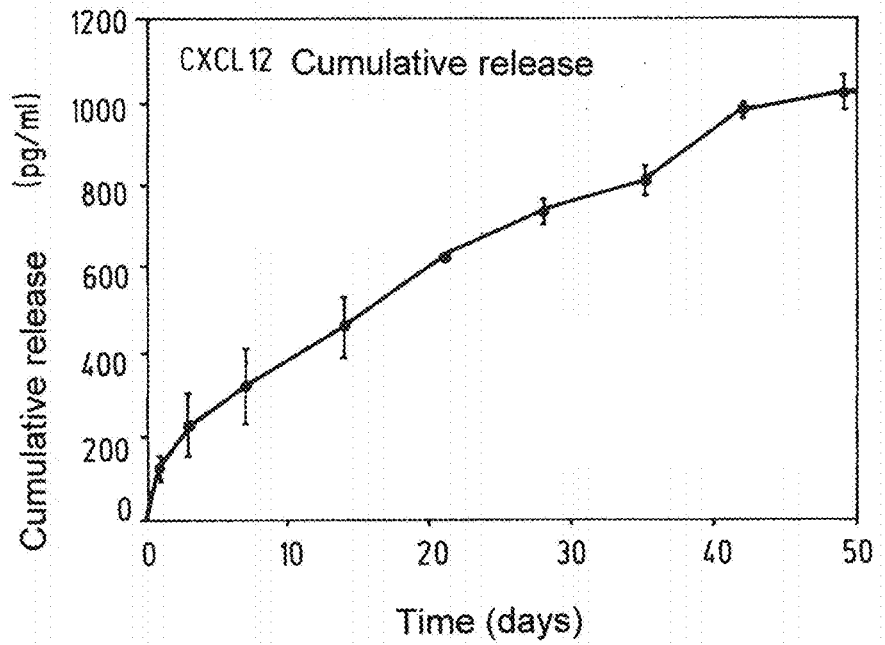
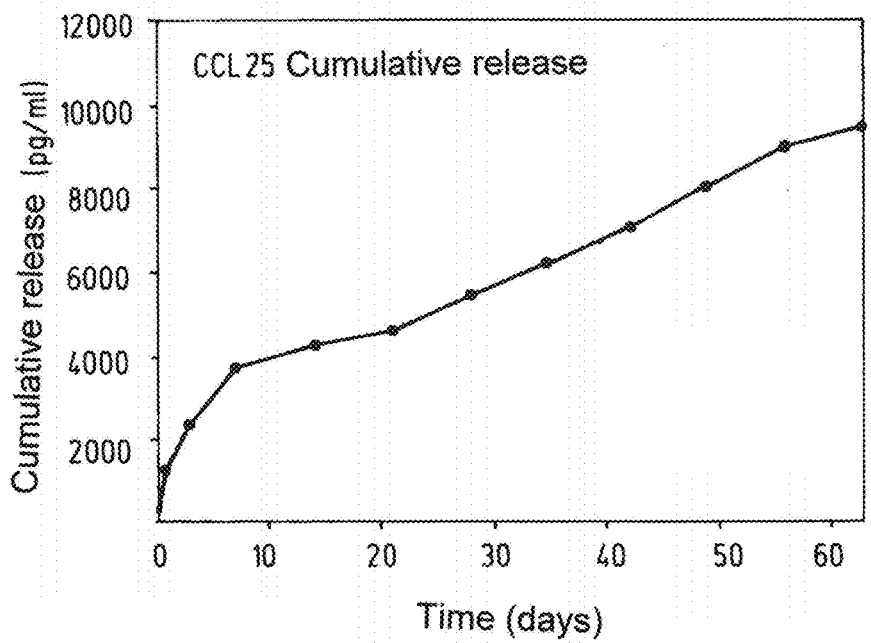
Fig.4

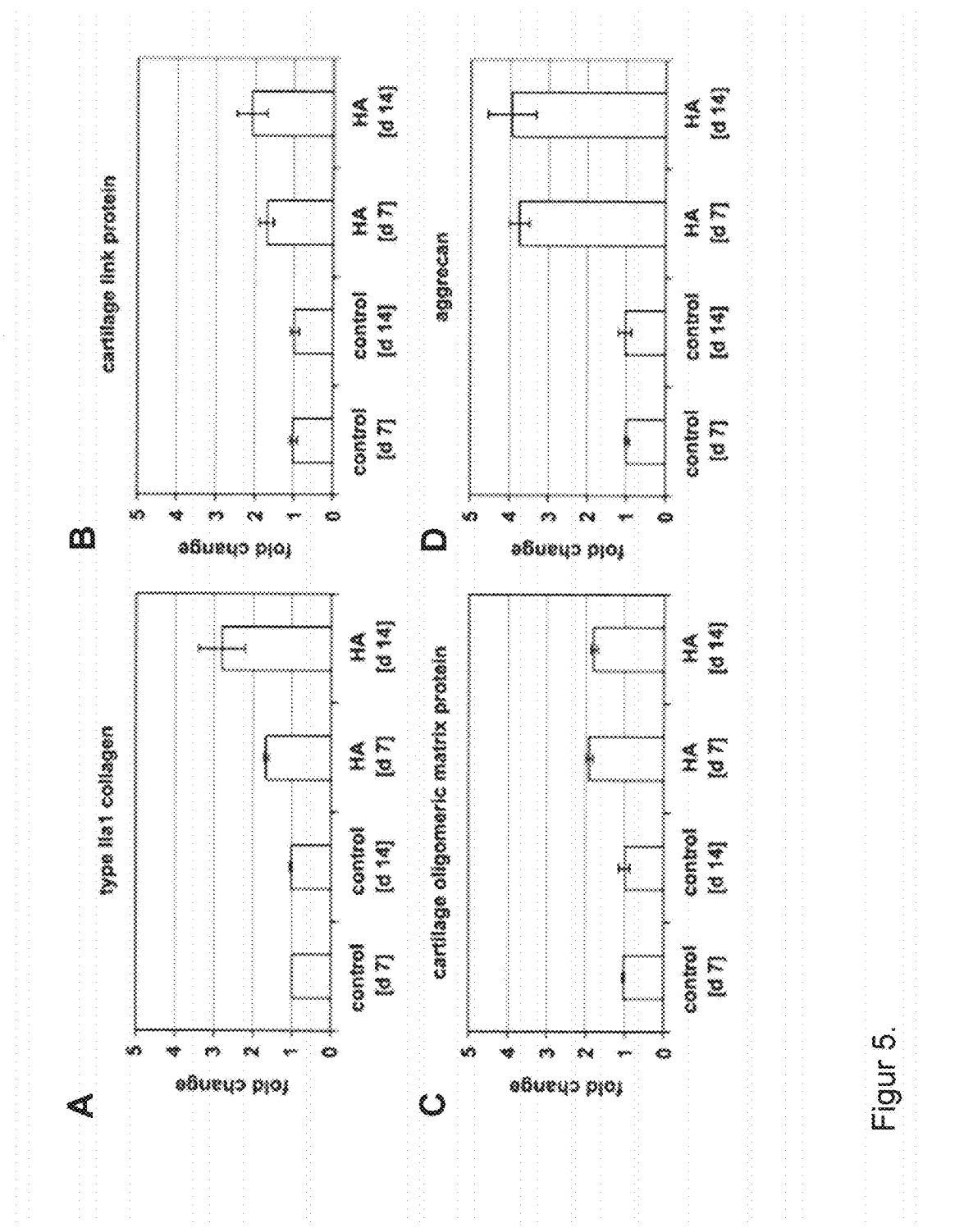
Figur 5.

USE OF CYTOKINE-RELEASING, BIODEGRADABLE PARTICLES IN HYALURONIC ACID FOR THE TREATMENT OF CARTILAGE DEFECTS, IN PARTICULAR OF OSTEOARTHROSIS

CROSS REFERENCE TO RELATED APPLICATIONS

This is a U.S. §371 National Phase of PCT/EP2011/071412, filed Nov. 30, 2011, which claims priority to German Patent Application No. DE102010062288, filed Dec. 1, 2010, the entirety of which are incorporated herein by reference.

According to the Federal Office of Statistics, osteoarthritis (OA, wear and tear of the joints), particularly osteoarthritis of the knee and hip joints, is one of the 30 most frequent individual diagnoses made during hospital stays. In the year 2007, around 15 million arthritis patients were under treatment. The demographic growth which is expected to take place in Germany means that there is likely to be a further increase in the demand for such treatment in future.

Despite some available treatments, there has so far not been a form of treatment which can actually arrest or even reverse the disease process of osteoarthritis. Treatments such as autologous chondrocyte transplantation or the implantation of cell-free implants have been developed for small local cartilage defects. However, these treatments are unable to stop further cartilage degeneration and are also not suitable for use with osteoarthritis defects which cover larger areas. Sooner or later, osteoarthritis usually requires the replacement of joints. Every year, around 420,000 arthritis operations involving total joint replacements are performed. The necessary outpatient and inpatient care is very expensive. According to the calculations of the Federal Office of Statistics, around 7 billion euros were spent on the treatment of arthritis in the year 2002. Moreover, this chronic degenerative disease also gives rise to considerable national expenditure as a result of the inability to work, early retirement and rehabilitation of people affected by the disease.

For advanced osteoarthritis defects, there are other treatment concepts such as the administration of glucosamine/chondroitin and dietary therapies as well as total joint replacements and pain therapy. However, the efficacy of such therapies has not been well substantiated up until now. Only the intra-articular administration of hyaluronic acid (abbreviated to HA), which is supposed to function as an additional 'joint lubricant', has shown a positive effect in prospective controlled studies. Further cartilage degeneration has been able to be prevented. Cartilage regeneration has not been proved.

There continues to be a need for further effective forms of therapy for the treatment of osteoarthritis which make it possible to stop cartilage degeneration and, where relevant, even the regeneration of diseased cartilage tissue and thus delay or even render unnecessary the implantation of total joint replacements.

The object of this invention is to reduce or prevent one or more of the disadvantages of the state-of-the-art technology. In particular, the object of the invention is to provide new efficacious drugs and treatment methods for osteoarthritis.

This invention is able to achieve this object by providing a composition which contains or consists of:

| | |
|---|---|
| 2-50 mg/ml | hyaluronic acid; |
| 0.1-500 mg/ml | biodegradable particles with an average particle diameter of 1 nm-500 µm; |
| 1 pg/ml-10 µg/ml | cytokines, | with the details of the concentration relating to the total volume (w/v) of the composition in each case and with the cytokines being enclosed in the biodegradable particles.

The invention is based on the surprising finding that the simultaneous administration of hyaluronic acid and cytokines synergistically promotes the migration of cells which are involved with the formation of a healthy joint, for example mesenchymal stem and/or progenitor cells. As a result, the recruitment of healthy cells for tissue regeneration in joints with cartilage defects, for example joints affected by osteoarthritis and joints with traumatic cartilage defects, is promoted and increased in a particularly beneficial way. The positive effect is, among other things, achieved by the cytokines being formulated in such a way that they are not released at once, but are released in a controlled way over a fairly long period of time. In the composition according to the invention, this is achieved by enclosing the cytokines in particles which are biodegradable. After administration into the body of a patient who is to be treated, the particles decompose over time and continuously release cytokines.

The administration of the composition according to the invention, particularly gel-like hyaluronic acid in combination with cytokine-releasing, biodegradable particles in the intra-articular space makes it possible to achieve a practical and promising expansion of the treatment options for cartilage defects, e.g. traumatic cartilage defects and osteoarthritis. As well as delaying cartilage degeneration by means of hyaluronic acid, the cytokine-releasing particles are also simultaneously able to exercise a regenerative effect on the damaged cartilage in the intra-articular space.

After the intra-articular administration of the composition according to the invention, hyaluronic acid delays further degeneration of the cartilage and promotes new cartilage formation as a result of its role as a 'joint lubricant' and a chondrogenic factor. The concomitant and controlled release of cytokines lasting several days or even weeks specifically stimulates stem and/or progenitor cells and/or attracts the latter so that these types of cell accumulate in the region of the osteoarthritis or the diseased region of the joint. In so doing, advantage is particularly taken of the fact that the new formation of cartilage which is mediated by hyaluronic acid plays a supportive role in the recruitment and colonisation of stem and/or progenitor cells. It was also able to be shown that the combined administration of hyaluronic acid and cytokines has a synergistic effect on the recruitment of stem and/or progenitor cells. Thus, a specific accumulation of the body's own stem and/or progenitor cells in the diseased joint is achieved as a result of the injection of the composition according to the invention, while progression of cartilage degeneration is delayed and regeneration of the damaged cartilage tissue is stimulated as a result of combination with the simultaneous local administration of hyaluronic acid.

The composition according to the invention contains hyaluronic acid in a concentration of 2-50 mg/ml with regard to the total volume (w/v) of the composition. It is preferable if the composition according to the invention contains 5-30 mg/ml of hyaluronic acid, it is particularly preferable if it contains 10-20 mg/ml and it is especially preferable if it contains 10 or 20 mg/ml with regard to the total volume (w/v) of the composition in each case.

Those skilled in the art are familiar with methods for obtaining or producing hyaluronic acid. Hyaluronic acid is usually extracted from tissues or produced by means of biotechnological processes, for example fermentation.

The half-life of hyaluronic acid after administration into the tissues depends on the molar mass of the hyaluronic acid. In order to ensure a particularly beneficial half-life of hyaluronic acid after the administration of the composition according to the invention, the composition according to the invention contains hyaluronic acid with an average mean molar mass of at least 200 kDa, preferably 250 kDa to 7,000 kDa, particularly preferably 500 kDa to 4,000 kDa and especially preferably 1,000 kDa to 3,000 kDa.

The composition according to the invention contains biodegradable particles which enclose the cytokines. In this way, the composition according to the invention has the particles in a concentration of 0.1 mg/ml to 500 mg/ml, preferably in a concentration of 1 mg/ml to 300 mg/ml and particularly preferably in a concentration of 5 mg/ml to 200 mg/ml with regard to the total volume (w/v) of the composition in each case. A composition according to the invention which contains biodegradable particles in a concentration of 50 mg/ml is particularly good as an injectable solution for intra-articular injection into the joints which are to be treated. Conversely, a composition according to the invention which contains biodegradable particles in a concentration of 200 mg/ml is particularly suitable for the production of a paste or a gel for arthroscopic treatment.

The biodegradable particles have an average mean particle diameter of 1 nm to 500 μm, preferably 10 nm to 200 μm and particularly preferably 100 nm-50 μm.

By the term 'biodegradable' is understood particles which decompose over time and which are finally resorbed and/or excreted after implantation in a human or animal body or tissue. For this purpose, the particles of the composition according to the invention can consist of a biocompatible, biodegradable polymer or can contain this. By biocompatibility or physical tolerance is understood the ability of a polymer to produce an appropriate tissue response in the case of a specific application. In other words, a polymer is biocompatible if the polymer does not produce any intolerable adverse reactions after implantation in the body or tissue.

In the sense of the invention, the term 'biodegradable' refers to polymers or particles which decompose/restructure over time in a physiological environment, so that the polymer or particle is no longer available or is mostly no longer available after implantation. Artificial plasma as required for biodegradation tests according to EN ISO 10993-15:2000 serves as a test medium for the purposes of testing the degradation behaviour of possible polymers or particles (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l and $NaH_2PO_4$ 0.026 g/l). The artificial plasma referred to in EN ISO 10993-15:2000 corresponds to a sanguinous medium and thus represents an opportunity for the reproduction of a physiological environment in the sense of the invention. A sample of the polymer or particle to be examined is stored for this purpose in a sealed container with a defined quantity of the test medium at 37° C. On the basis of the expected degradation behaviour, samples are taken at intervals of time ranging from a few hours to several months and are examined in a known way for traces of degradation.

Suitable biocompatible and biodegradable polymers include polymers or co-polymers which contain or consist of a lactic acid (LA) and/or glycolic acid (GA) monomer, polylactic acid (PLA), polyglycolic acid (PGA), polylactide-co-glycolide (PLGA), polyethylene glycol (PEG), PLGA-PEG, polycaprolactones, polycarbonates, polyamides, polyanhydrides, chitosans, dextranes, cyclodextrins and/or fibrinogen. It is particularly preferable if the biodegradable particles contain or consist of PLGA, with the PLGA end groups being able to be modified. The PLGA can be used in a D-, L- or D-/L configuration. It is preferable if the PLGA has a molar mass of 5 kDa to 100 kDa and it is particularly preferable if the PLGA has a molar mass of 15 kDa.

Enclosed in the biodegradable particles, the composition according to the invention contains 1 pg/ml to 10 pg/ml of cytokines, preferably 10 pg/ml to 1 μg/ml of cytokines and particularly preferably 100 pg/ml to 100 ng/ml of cytokines with regard to the total volume (w/v) of the composition in each case. By cytokines is understood proteins which exert a regulating function on the growth, migration and/or differentiation of cells. Cytokines include both growth factors as well as chemokines and differentiation factors. According to the invention, it is specifically possible to use cytokines which stimulate and/or activate mesenchymal stem and/or progenitor cells. Preferred cytokines are growth and differentiation factors of the TGF (transforming growth factor), BMP (bone morphogenetic protein), GDF (growth differentiation factor), FGF (fibroblast growth factor), CTGF (connective tissue growth factor), PDGF (platelet derived growth factor), VEGF (vascular endothelial growth factor), EGF (epidermal growth factor), IGF (insulin-like growth factor) and/or CDMP (cartilage-derived morphogenetic protein) family. Preferred chemokines are CCL-1, -2, -3, -4, -5, -7, -8, -11, -13, -14, -15, -16, -17, -19, -20, -21, -22, -23, -24, -25, -26, -27, -28, CXCL-1, -2, -3, -5, -6, -7, -8, -9, -10, -11, -12, -13, -16, CX3CL-1, XCL-1 and/or XCL-2. It is particularly preferable if cytokines CXCL-10, CXCL-12, CCL25 and/or XCL-1 are used or a mixture containing one, several or all four of these cytokines. In particular, cytokines CXCL-12 and/or CCL-25 can be used in the composition according to the invention.

The biodegradable cytokine-carrying particles can be produced in a known way. Suitable methods of production result from the choice of the particular materials of which the particles are composed, in particular the choice of biocompatible, biodegradable polymers. The usual methods of production include production by formulation in emulsion (e.g. w/o/w-, s/o/w and o/w emulsion), with the cytokine usually being present in a dissolved form in the aqueous phase and being finely distributed in an organic polymer phase, and then solvent vaporisation, production by means of phase separation, spray drying and other methods such as 'supercritical fluid technology'.

The particles can be characterised by particularly advantageous release behaviour, with the release behaviour of cytokines from the particles essentially being determined by the size and composition of the particles as well as the concentration and choice of the cytokines which they enclose. It is preferable if the particles of the composition according to the invention are characterised by the continuous release of cytokines from the particles over several days. In particular, release can be essentially linear after an initial start-up phase lasting 24 hours to 36 hours. It is particularly preferable if the particles of the composition according to the invention are characterised by the release of cytokines at a rate of not more than 50% by weight of the enclosed cytokines per 24 hours and it is especially preferable if the particles are released at a rate of not more than 50% by weight of the enclosed cytokines per 48 hours.

The composition according to the invention can also contain fibrinogen. The addition of fibrinogen has the effect of ensuring that the composition is stabilised after implantation and is not able to be quickly eroded. As a result of contact with the blood, the fibrinogen quickly hardens and thus fixes the composition in place at the required location in the joint. This is particularly desirable if the composition is administered arthroscopically to the lesion in the form of a gel or paste. As a result, it is possible to treat or fill small or large local osteoarthrotic cartilage defects with the composition according to the invention in the form of a paste or gel by means of minimally invasive arthroscopic techniques. It is preferable if the composition according to the invention contains 10 mg/ml to 300 mg/ml of fibrinogen and particularly if it contains 70 mg/ml to 110 mg/ml with regard to the total volume (w/v) of the composition in each case.

The components of the composition according to the invention, particularly hyaluronic acid, and the particles loaded with cytokines can be dissolved, emulsified or suspended in a solvent. It is preferable if the solvent is an aqueous solvent such as water. As the composition according to the invention is suitable for use as a medicine or as an active ingredient of a medicine, it is particularly advantageous if the solvent is an infusible aqueous solution, for example an isotonic saline solution. The infusible aqueous solution and in particular the isotonic saline solution can be buffered in order to keep the pH at a physiologically acceptable level or to restore a physiological pH. Those skilled in the art are familiar with suitable buffers.

This invention also relates to a pharmaceutical composition which contains a composition according to the invention and one or more pharmaceutically tolerable excipients. The term 'excipient' is here used to describe all other ingredients except the composition according to the invention. The choice of the excipient or the excipients is largely based on the particular kind of administration. With regard to this, excipients can, for example, be used for the formulation and/or stabilisers, preservatives, viscosity-adjusting excipients, antioxidants, colouring agents, binding agents, emulsifiers, humectants, solvents, fillers, salts, carbohydrates and/or buffer substances can be used. It is preferable if the excipients are salts, carbohydrates and/or buffer substances which are suitable for parenteral administration, particularly implantation in the body of an individual who is to be treated.

In a particular embodiment, the pharmaceutical composition according to the invention is designed for intra-articular injection. For this purpose, the concentration of the particles in the pharmaceutical composition is 50 mg/ml and that of hyaluronic acid is 10 mg/ml with regard to the total volume (w/v) of the pharmaceutical composition in each case. The pharmaceutical composition is preferably available as an injectable aqueous solution; it is particularly preferable if the ingredients of the composition according to the invention are dissolved, emulsified or suspended in an isotonic and, where relevant, buffered saline solution.

In another embodiment, the pharmaceutical composition according to the invention is designed for arthroscopic treatment. It is preferable if the pharmaceutical composition is available for this purpose in the form of a gel or paste. With regard to this, the concentration of particles in the pharmaceutical composition can be 200 mg/ml and that of the hyaluronic acid can be 20 mg/ml with regard to the total volume (w/v) of the pharmaceutical composition in each case. The pharmaceutical composition can also contain 70-110 mg/ml of fibrinogen with regard to the total volume (w/v) of the pharmaceutical composition.

The composition according to the invention or the pharmaceutical composition according to the invention can be used for the treatment and/or prevention of cartilage defects, for example traumatic cartilage defects or osteoarthritis, particularly for the treatment and/or prevention of osteoarthritis in joints, for example in knee, ankle, shoulder and/or hip joints. It is preferable if the composition according to the invention or the pharmaceutical composition according to the invention is used for the treatment and/or prevention of cartilage defects in mammals, particularly people and/or working animals or pets.

This invention also relates to the composition according to the invention or the pharmaceutical composition according to the invention being used in the treatment and/or prevention of cartilage defects, for example traumatic cartilage defects or osteoarthritis, particularly osteoarthritis in the knee, ankle, shoulder and/or hip joints.

This invention also relates to a method for the treatment and/or prevention of cartilage defects, for example traumatic cartilage defects or osteoarthritis, with an individual who requires such a treatment being administered an efficacious dose of the composition according to the invention or the pharmaceutical composition according to the invention.

According to this invention, it is preferable if the composition or the pharmaceutical composition is administered in an efficacious dose. An 'efficacious dose' is the dose of the composition according to the invention which produces a measurable therapeutic effect with regard to the disease in question when administered to an individual. In the case of this invention, an efficacious dose is the dose of the composition according to the invention which produces a therapeutic effect with regard to the cartilage defects which are to be treated. It is preferable if the composition according to the invention is administered in a dose of 0.1 to 10 ml per joint to be treated and preferably from 1 ml to 3 ml per joint to be treated. In order to ensure that the treatment is particularly successful, the joint which is to be treated is treated with the composition according to the invention more than once. It is preferable if the treatment of an affected joint is repeated one to three times, so that it is possible to have a total of two to four treatments per joint and treatment cycle. It is preferable if the repeated administration takes place at intervals of 4 to 9 days and it is particularly preferable if the repeated administration takes place at intervals of 7 days.

This invention also relates to the use of a composition according to the invention or a pharmaceutical composition according to the invention for the production of a medicine for the treatment and/or prevention of cartilage defects, for example traumatic cartilage defects or osteoarthritis, particularly osteoarthritis of the knee, ankle, shoulder and/or hip joints, with the medicine being designed for the administration of 0.1 ml to 10 ml and preferably 1 ml to 3 ml of the composition per joint to be treated and, where relevant, repetition of the treatment one to three times at intervals of 4 to 9 days.

The treatment of a joint affected by osteoarthosis with a composition according to the invention or with a pharmaceutical composition according to the invention can particularly be combined with other forms of therapy for the treatment of osteoarthritis. In particular, the form of administration of the pharmaceutical composition according to the invention as a paste or gel for arthroscopic administration can be administered after arthroscopic treatment which includes microfracturation and/or Pridie drilling.

In another embodiment, this invention relates to a pre-filled syringe which is filled with an injectable suspension which contains or consists of a composition according to the invention or a pharmaceutical composition according to the invention. This prefilled syringe can be used for the treatment and/or prevention of cartilage defects, for example traumatic cartilage defects or osteoarthritis, particularly osteoarthritis of the knee, ankle, shoulder and/or hip joints.

The invention is clarified in more detail below with exemplary embodiments.

FIGURES

Figure 2:
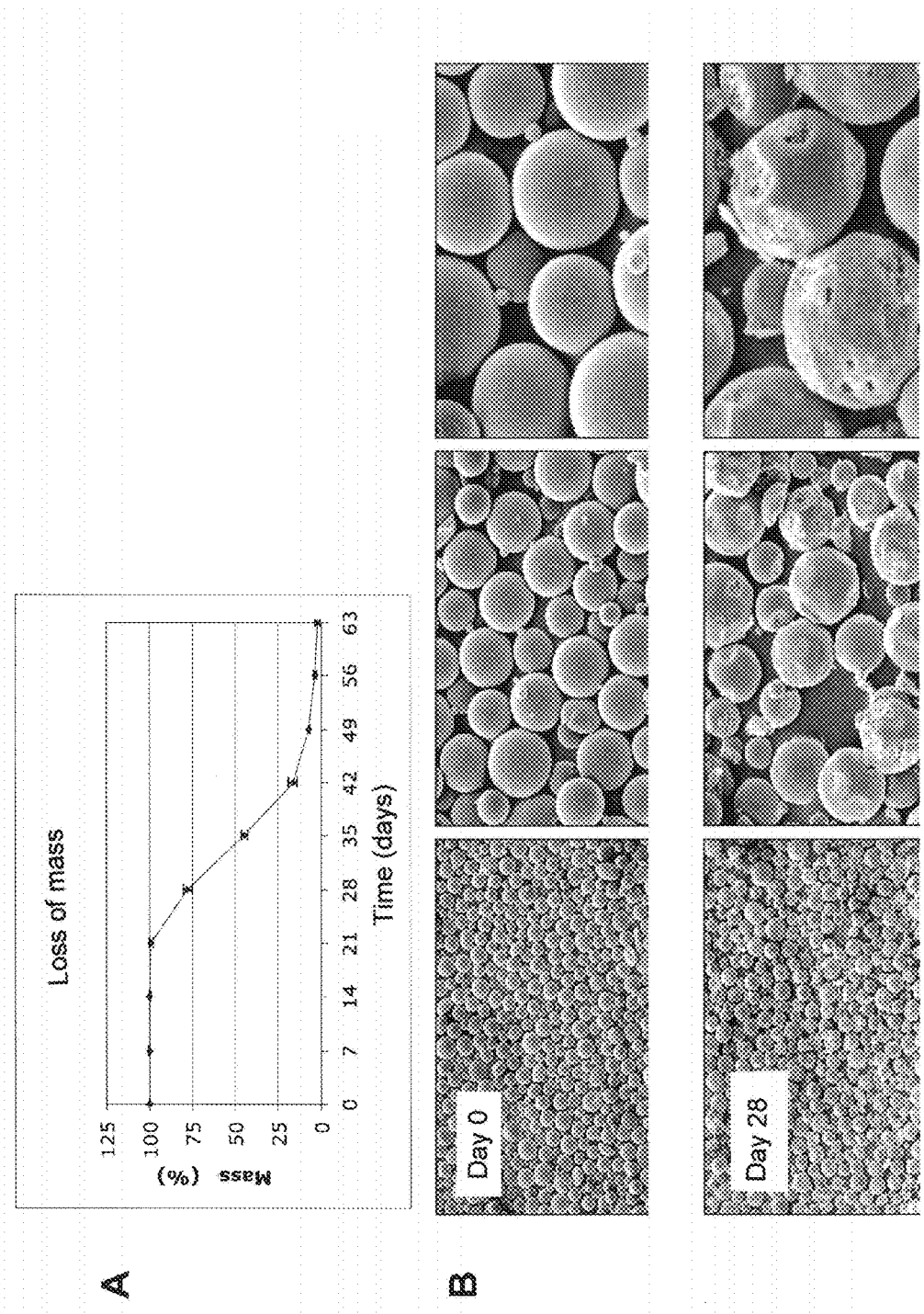
Figure 3:
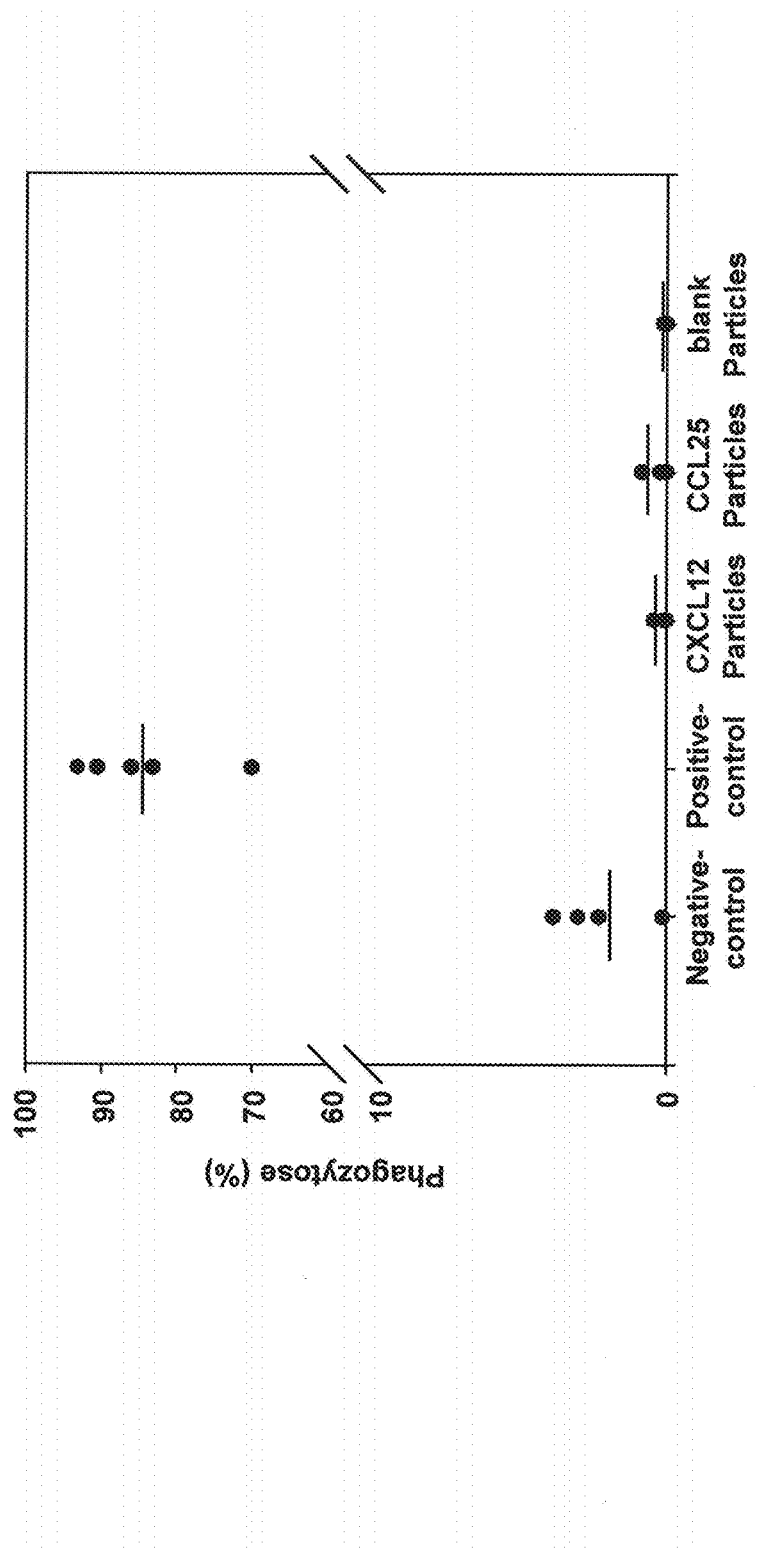
Figure 6A:
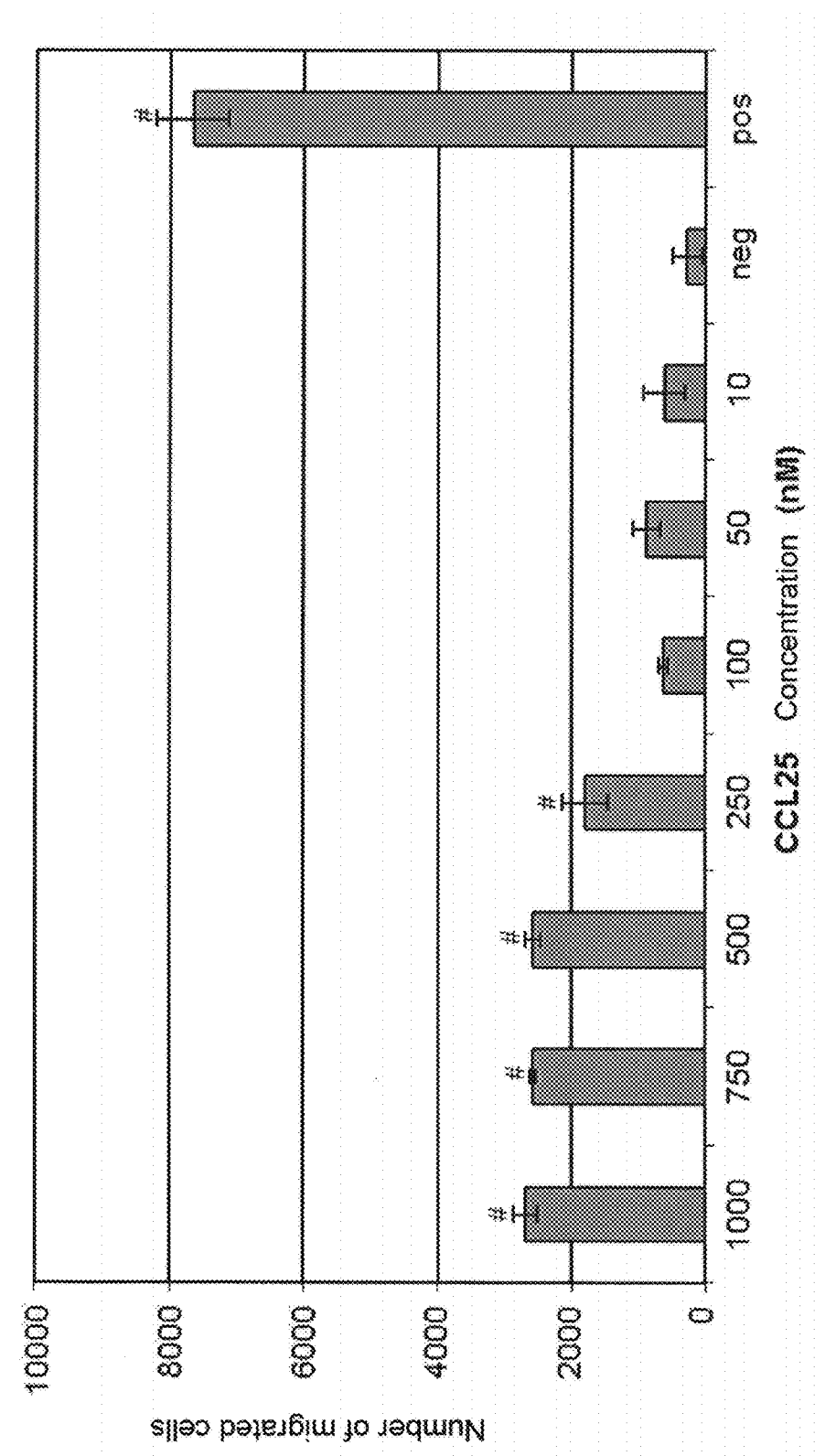
Figure 6B:
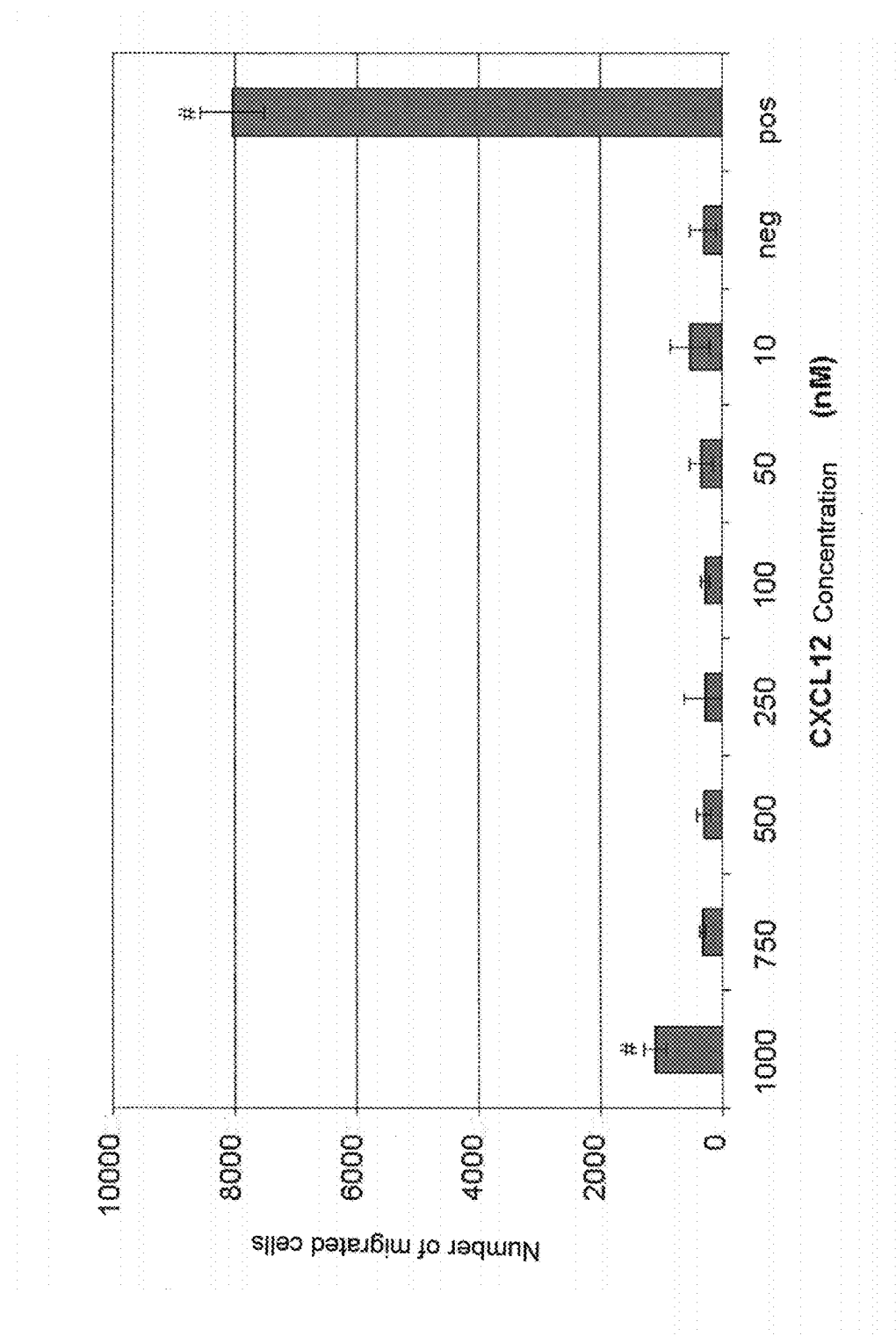
Figure 7:
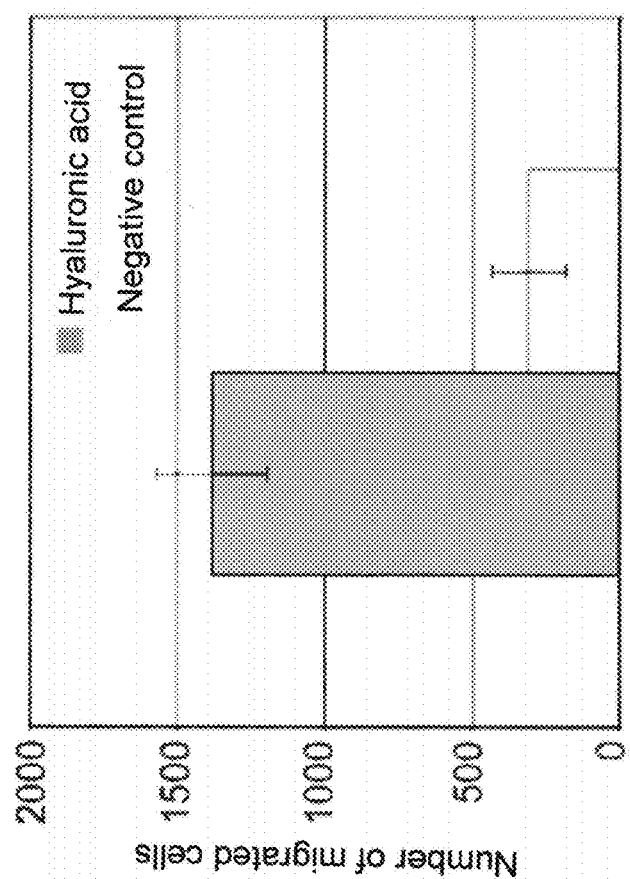
Figure 8:
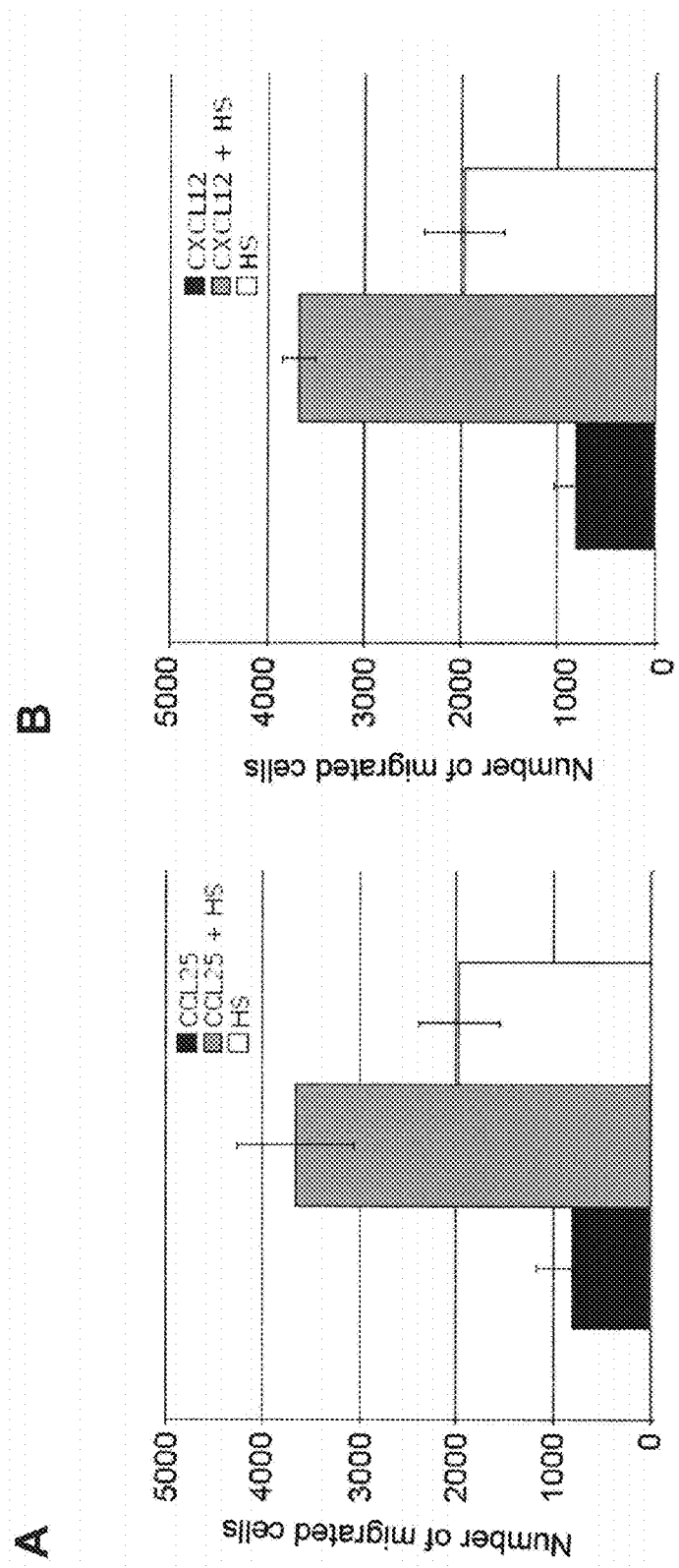

There is shown:

FIG. 1: the size distribution and morphology of the PLGA chemokine particles produced: (A) size distribution curve, (B) and (C) representative scanning electron microscope images;

FIG. 2: the degradation of the PLGA chemokine particles in an aqueous environment: (A) loss of mass of particles over time and (B) morphological changes of particles on the basis of scanning electron microscope investigations;

FIG. 3: a phagocytosis assay of chemokine-loaded particles;

FIG. 4: cumulative release kinetics from PLGA particles over several weeks for chemokines CXCL12 (A) and CCL25 (B);

FIG. 5: the expression of different typical cartilage genes is highly regulated with the chondrogenic differentiation of mesenchymal stem and progenitor cells with hyaluronic acid, d=day; (A) collagen type II, (B) cartilage link protein, (C) cartilage oligomeric matrix protein and (D) aggrecan;

FIG. 6: a chemotaxis assay with mesenchymal stem and progenitor cells subject to stimulation with different concentrations of CCL25 (A) and CXCL12 (B);

FIG. 7: a chemotaxis assay: hyaluronic acid stimulates the migration of mesenchymal stem and progenitor cells; and FIG. 8: a chemotaxis assay: the combination of HA and chemokine CCL25 or CXCL12 synergistically stimulates the migration of mesenchymal stem and progenitor cells; HA, hyaluronic acid; (A) combination of HA with CCL25, (B) combination of HA with CXCL12.

The invention claimed is:

1. A composition comprising:

| | |
|---|---|
| 2-50 mg/ml | hyaluronic acid; |
| 0.1-500 mg/ml | biodegradable particles with an average mean particle diameter of 1 nm-500 μm; |
| 1 pg/ml-10 μg/ml | CCL25 cytokine; | wherein the details of the concentration in each case relate to the total volume (w/v) of the composition and wherein the CCL25 cytokine is enclosed in the biodegradable particles and the combination of hyaluronic acid and CCL25 cytokines synergistically promotes the migration of mesenchymal stem or progenitor cells.

2. The composition according to claim 1, characterised in that the composition comprises 5-30 mg/ml of hyaluronic acid.

3. The composition according to claim 1, characterised in that the composition comprises 1-300 mg/ml of particles.

4. The composition according to claim 1, characterised in that the particles have an average mean particle size of 10 nm-200 μm.

5. The composition according to claim 1, characterised in that the composition comprises the cytokines enclosed in the particles in a concentration of 10 pg/ml-1 μg/ml.

6. The composition according to claim 1, characterised in that the cytokines are CXCL10, CXCL12, CCL25 or XCL1 or a mixture containing one or several of these.

7. The composition according to claim 1, characterised in that the particles contain or consist of a biocompatible, biodegradable polymer.

8. The composition according to claim 1, characterised in that the particles contain or consist of a biocompatible, biodegradable polymer, wherein the biocompatible, biodegradable polymer is chosen from polymers or co-polymers which contain a PLA and/or a PGA monomer, PLGA, PLGA-PEG, polycaprolactones, polycarbonates, polyamides, polyanhydrides, PEG, chitosans, dextranes, cyclodextrins and/or fibrinogen.

9. The composition according to claim 1, characterised in that the composition also comprises an aqueous solvent.

10. The composition according to claim 1, characterised in that the composition also comprises 10-300 mg/ml of fibrinogen.

11. A pharmaceutical composition containing a composition according to claim 1 and at least one pharmaceutically tolerable excipient.

12. The pharmaceutical composition according to claim 11 for the intra-articular injection, characterised in that the concentration of the particles in the pharmaceutical composition is 50 mg/ml and that of hyaluronic acid is 10 mg/ml.

13. The pharmaceutical composition according to claim 11 for arthroscopic treatment, characterised in that the concentration of particles in the pharmaceutical composition is 200 mg/ml, that of hyaluronic acid is 20 mg/ml and the pharmaceutical composition contains 70-110 mg/ml of fibrinogen.

14. Method of treatment and/or prevention of cartilage defects, for example traumatic cartilage defects or osteoarthritis, particularly osteoarthritis of the knee, ankle, shoulder and/or hip joints, wherein a person in need of such treatment is administered an effective dose of a composition according to claim 1 or a pharmaceutical composition according to claim 11.

15. Method of treatment and/or prevention of cartilage defects, for example traumatic cartilage defects or osteoarthritis and particularly osteoarthritis of the knee, ankle, shoulder and/or hip joints, wherein a person in need of such treatment is administered an effective dose of a pharmaceutical composition according to claim 11, characterized in that 0.1 to 10 ml of the pharmaceutical composition are administered per treatment and, where relevant, treatment is repeated one to three times at intervals of 4 to 9 days in each case.

* * * * *